(12) United States Patent
Denis et al.

(10) Patent No.: US 9,719,401 B2
(45) Date of Patent: Aug. 1, 2017

(54) SENSOR MOUNTING APPARATUS

(71) Applicant: Caterpillar Inc., Peoria, IL (US)

(72) Inventors: Andrew M. Denis, Peoria, IL (US); Eric A. Scott, Peoria, IL (US); Eric P. Spaeth, Pekin, IL (US); Jianping Pan, Dunlap, IL (US); Katherine D. Driscoll, Dunlap, IL (US); Timothy J. Alcenius, Dunlap, IL (US); Kimberly M. Stanek, Dunlap, IL (US)

(73) Assignee: Caterpillar Inc., Peoria, IL (US)

( * ) Notice: Subject to any disclaimer, the term of this patent is extended or adjusted under 35 U.S.C. 154(b) by 335 days.

(21) Appl. No.: 14/298,173

(22) Filed: Jun. 6, 2014

(65) Prior Publication Data
US 2015/0354431 A1 Dec. 10, 2015

(51) Int. Cl.
F01N 13/00 (2010.01)
G01N 33/00 (2006.01)
F01N 3/00 (2006.01)

(52) U.S. Cl.
CPC ......... F01N 13/008 (2013.01); F01N 3/005 (2013.01); G01N 33/0037 (2013.01); *F01N 2560/026* (2013.01); *Y02T 10/20* (2013.01)

(58) Field of Classification Search
CPC .............................. F01N 13/008; F01N 3/005
See application file for complete search history.

(56) References Cited

U.S. PATENT DOCUMENTS

| 7,818,964 | B2 | 10/2010 | Muramatsu et al. |
| 8,057,741 | B2 | 11/2011 | Gustin |
| 8,635,864 | B2 | 1/2014 | Yamamoto |
| 2006/0042946 | A1* | 3/2006 | Tsukahara .......... G01N 27/4077 204/424 |
| 2007/0277605 | A1* | 12/2007 | Fouts .................. G01D 11/245 73/431 |
| 2013/0161112 | A1 | 6/2013 | Grzesiak et al. |
| 2013/0213013 | A1 | 8/2013 | Mitchell et al. |

FOREIGN PATENT DOCUMENTS

EP 2148057 9/2011

* cited by examiner

*Primary Examiner* — Ryan Walsh
(74) *Attorney, Agent, or Firm* — Bookoff, McAndrews PLLC

(57) ABSTRACT

A boss configured to mount a nitrous oxide sensor in an exhaust conduit is disclosed. The boss includes a first tier configured to contact with an exterior surface of the exhaust conduit, the first tier defined by a first diameter and a first height. The boss also includes a second tier extending from the first tier. The second tier is configured to be disposed within an interior space defined within the exhaust conduit. The second tier is defined by a second diameter and a second height. Further, the second diameter is sized smaller than the first diameter. The boss further includes a condensation protection feature configured to direct condensation away from the nitrous oxide sensor.

15 Claims, 8 Drawing Sheets

SENSOR MOUNTING APPARATUS

TECHNICAL FIELD

The present disclosure relates to a sensor mounting apparatus; and more to a mounting structure for a nitrogen oxide sensor associated with an exhaust system.

BACKGROUND

A Nitrogen Oxide (NOx) sensor may be positioned at various locations in an engine exhaust system, in order to measure a concentration of NOx in exhaust gases exiting an engine. For example, the NOx sensor may be positioned at an exhaust outlet of an aftertreatment system, and/or downstream or upstream of a Selective Catalytic Reduction (SCR) module with respect to a direction of flow of the exhaust gas.

Sometimes, the NOx sensors disposed within the exhaust outlet may get damaged due to entry of water or debris into the exhaust outlet. For example, water in the form of condensed water vapor or rain water may enter into the exhaust outlet and contact a sensing element of the NOx sensor. The water contacting the NOx sensor may damage the sensing element of the NOx sensor. Damage of the sensing element may require the NOx sensors to be replaced.

U.S. Pat. No. 7,818,964 discloses an exhaust system for a motorcycle having an engine mounted on a front half of a body frame of the motorcycle. The system includes a plurality of first exhaust pipes extending from exhaust ports of the engine, a collecting section at which the first exhaust pipes are collected, a second exhaust pipe including a substantially straight portion connected to a downstream side of the collecting section and disposed under a crankcase of the engine, an expansion chamber connected to a downstream side of the second exhaust pipe and located under a rear wheel suspension arranged behind the engine, an exhaust outlet disposed on a most downstream portion of the expansion chamber, and an exhaust throttle valve and an exhaust gas sensor disposed on the straight portion of the second exhaust pipe.

SUMMARY OF THE DISCLOSURE

In one aspect of the present disclosure, a boss configured to mount a nitrous oxide sensor in an exhaust conduit is disclosed. The boss includes a first tier configured to contact with an exterior surface of the exhaust conduit, the first tier defined by a first diameter and a first height. The boss also includes a second tier extending from the first tier. The second tier is configured to be disposed within an interior space defined within the exhaust conduit. The second tier is defined by a second diameter and a second height. Further, the second diameter is sized smaller than the first diameter. The boss further includes a condensation protection feature configured to direct condensation away from the nitrous oxide sensor.

In another aspect of the present disclosure, an exhaust conduit is disclosed. The exhaust conduit includes an exterior surface having an opening thereon. The exhaust conduit also includes a boss disposed within the opening. The boss is configured to receive a nitrous oxide sensor therein. The boss includes a first tier mounted in contact with the exterior surface of the exhaust conduit. The boss includes a second tier extending from the first tier. The second tier projects into an interior space of the exhaust conduit. The boss further includes a condensation protection feature configured to direct condensation away from the nitrous oxide sensor.

In yet another aspect of the present disclosure, a boss configured to mount a nitrous oxide sensor in an exhaust conduit is disclosed. The boss includes a first tier configured to contact with an exterior surface of the exhaust conduit, the first tier defined by a first diameter and a first height. The boss also includes a second tier extending from the first tier. The second tier is configured to be disposed within an interior space defined within the exhaust conduit. The second tier is defined by a second diameter and a second height. Further, the second diameter is sized smaller than the first diameter. The boss further includes a trumpet shaped section attached to the second tier of the boss. The trumpet shaped section has a sidewall. An outer face of the sidewall has a concave configuration. Further, the trumpet shaped section is configured to direct condensation away from the nitrous oxide sensor.

Other features and aspects of this disclosure will be apparent from the following description and the accompanying drawings.

DETAILED DESCRIPTION

Figure 1:
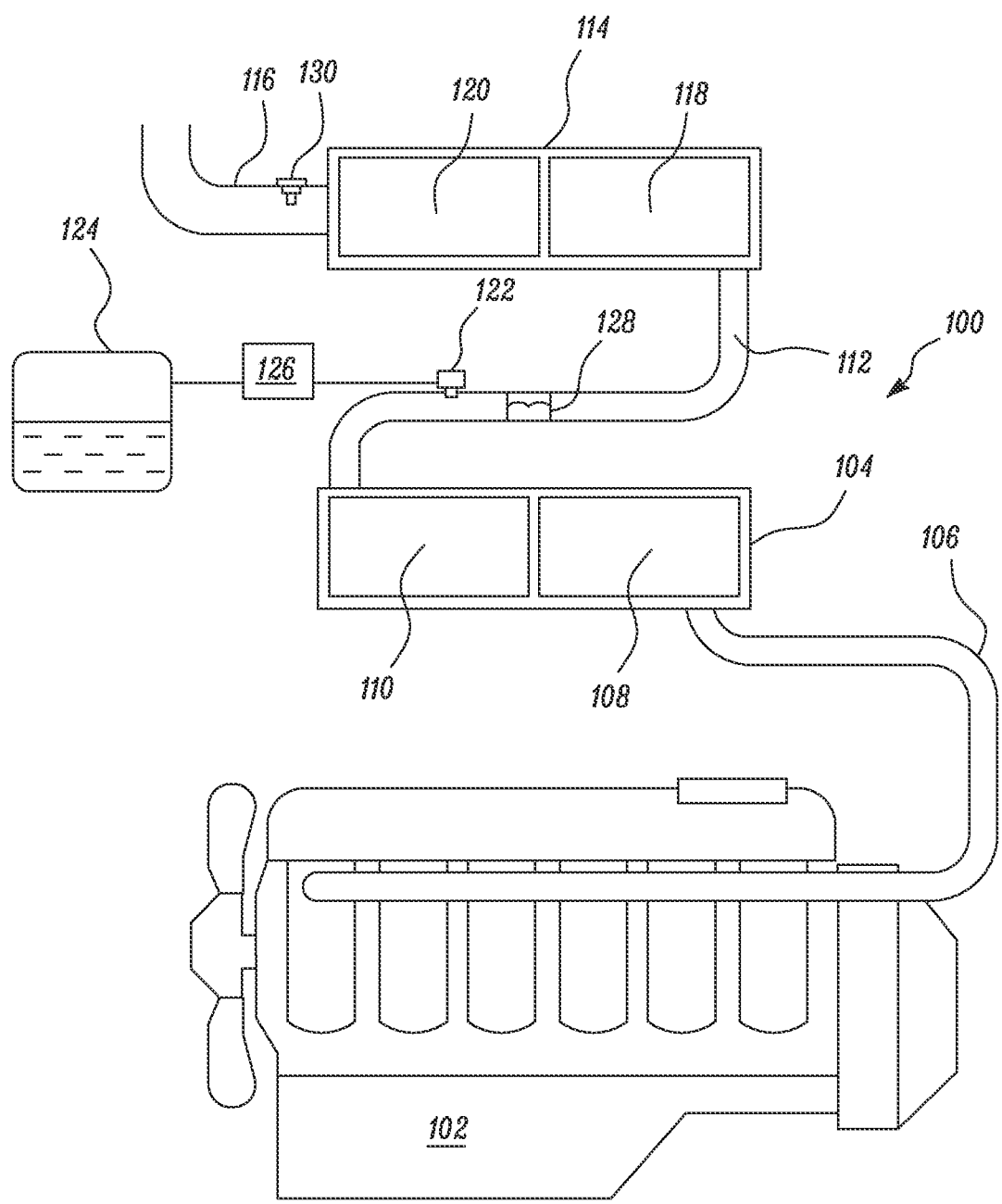
FIG. 1 is a block diagram of an exemplary aftertreatment system associated with an engine, according to one embodiment of the present disclosure.

Wherever possible, the same reference numbers will be used throughout the drawings to refer to the same or the like parts. FIG. 1 is a block diagram of an exemplary aftertreatment system 100 associated with an engine 102. The aftertreatment system 100 is configured to treat an exhaust gas flow exiting an exhaust manifold of the engine 102. The exhaust gas flow contains emission compounds that may include Nitrogen Oxides (NOx), unburned hydrocarbons, particulate matter and/or other combustion products known in the art. The aftertreatment system 100 may be configured to trap or convert NOx, unburned hydrocarbons, particulate matter, combinations thereof, or other combustion products in the exhaust gas flow before exiting an engine system.

The engine 102 may be associated with any machine. For example, the type of machine contemplated herein may be an earth-moving machine, such as a wheel loader, excavator, dump truck, backhoe, material handler, locomotive, paver, and the like. Apart from mobile machines, the machine contemplated may be a stationary or portable machine such as a generator set, an engine driving a gas compressor, or pump, and the like. Moreover, the machine may include or be associated with work implements such as those utilized and employed for a variety of tasks, including, for example, loading, compacting, lifting, brushing, and include, for example, buckets, compactors, forked lifting devices, brushes, grapples, cutters, shears, blades, breakers/hammers, augers, and others.

The engine 102 may include an internal combustion engine such as, for example, a reciprocating piston engine or a gas turbine engine. The engine 102 may be a spark ignition engine or a compression ignition engine such as a diesel engine, a homogeneous charge compression ignition engine, or a reactivity controlled compression ignition engine, or other compression ignition engine known in the art. The engine 102 may be fueled by gasoline, diesel fuel, biodiesel, dimethyl ether, alcohol, natural gas, propane, hydrogen, combinations thereof, or any other combustion fuel known in the art.

In the illustrated embodiment, the aftertreatment system 100 includes a first module 104 that is fluidly connected to an exhaust conduit 106 of the engine 102. During engine operation, the first module 104 is arranged to receive engine exhaust gas through the exhaust conduit 106. The first module 104 may contain various exhaust gas treatment devices such as, a diesel oxidation catalyst (DOC) 108 and a diesel particulate filter (DPF) 110, and other devices not shown herein. The first module 104 and the components therein are optional and may be omitted for various engine applications in which the exhaust treatment function provided by the first module 104 is not required.

In the illustrated embodiment, the exhaust gas provided to the first module 104 by the engine 102 may first pass through the DOC 108 and then through the DPF 110 before entering a transfer conduit 112. The transfer conduit 112 fluidly interconnects the first module 104 with a second module 114 such that the exhaust gases from the engine 102 may pass through the first and second modules 104, 114 in series before being passed through an exhaust outlet 116 that is connected downstream to the second module 114. The second module 114 encloses a Selective Catalytic Reduction (SCR) catalyst 118 and an Ammonia Oxidation Catalyst (AMOX) 120. The SCR catalyst 118 operates to treat the exhaust gas from the engine 102 in the presence of ammonia, which is provided after degradation of a urea-containing solution injected into the exhaust gas in the transfer conduit 112. The AMOX 120 is used to convert any ammonia slip from the downstream flow of the SCR catalyst 118 before the exhaust gases exit through the exhaust outlet 116.

More specifically, a reductant, for example, diesel exhaust fluid (DEF), is injected into the transfer conduit 112 by a reductant injector 122. The reductant is contained within a reductant tank 124 and is provided to the reductant injector 122 by a pump module 126. As the reductant is injected into the transfer conduit 112, the reductant mixes with the exhaust gas passing therethrough and is carried to the second module 114.

In order to promote mixing of the reductant with the exhaust gas, a mixer 128 may be disposed along the transfer conduit 112. The mixing of the reductant with the exhaust gas is not limited to a separate mixer 128 but may be accomplished with other known techniques such as a curved transfer conduit 112. The amount of the reductant that may be injected into the transfer conduit 112 may be appropriately metered based on engine operating conditions.

A Nitrogen Oxide Sensor (NOx) sensor 130 may be mounted at different locations of the aftertreatment system 100. In one example, the NOx sensor 130 may be mounted in the transfer conduit 112, downstream of the reductant injector 122 and upstream of the second module 114. Alternatively or additionally, the NOx sensor 130 is disposed on a surface of the exhaust outlet 116, downstream of the second module 114. The NOx sensor 130 is a high temperature device and generally includes a sensing element made of a ceramic material. The sensing element of the NOx sensor 130 is configured to contact the exhaust gases. The NOx sensor 130 is configured to measure a concentration of NOx present in the exhaust gas flow.

It should be noted that the aftertreatment system 100, that is the components and their connections disclosed herein is exemplary and does not limit the scope of the present disclosure. The aftertreatment system 100 may additionally include other components not described herein. Further, the design of the aftertreatment system 100 may vary based on the application.

Figure 2:
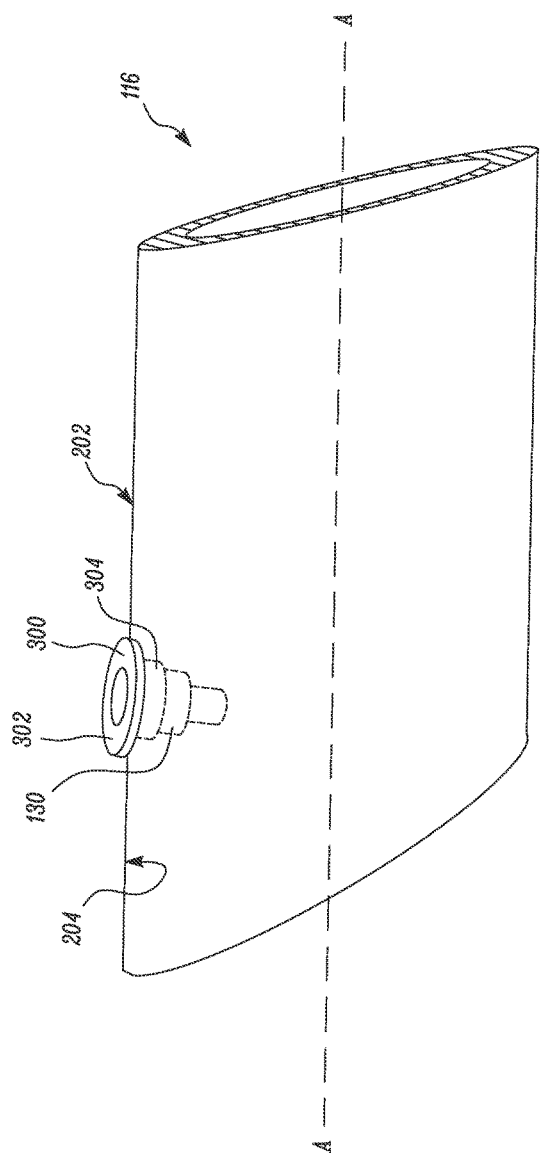
FIG. 2 is a perspective view of an exhaust outlet of the aftertreatment system, the exhaust outlet including a boss and a sensor.

FIG. 2 illustrates a portion of the exhaust outlet 116. The exhaust outlet 116 defines a centerline A-A. The NOx sensor 130 is mounted in the exhaust outlet 116 in a manner such that the NOx sensor 130 protrudes or projects into the exhaust outlet 116 wherein a sensing vector of the NOx sensor 130 is perpendicular to the centerline A-A.

A boss 300 is received within an opening provided on the exhaust outlet 116. The boss 300 is configured to mount the NOx sensor 130 in the exhaust outlet 116. The boss 300 may be threadably received within the opening of the exhaust outlet 116. Alternatively, the boss 300 may be affixed to the exhaust outlet 116 by welding, brazing, or any other similar attachment methods known in the art. The construction and structure of the boss 300 will now be described in detail, according to various embodiments of the present disclosure.

Figure 3:
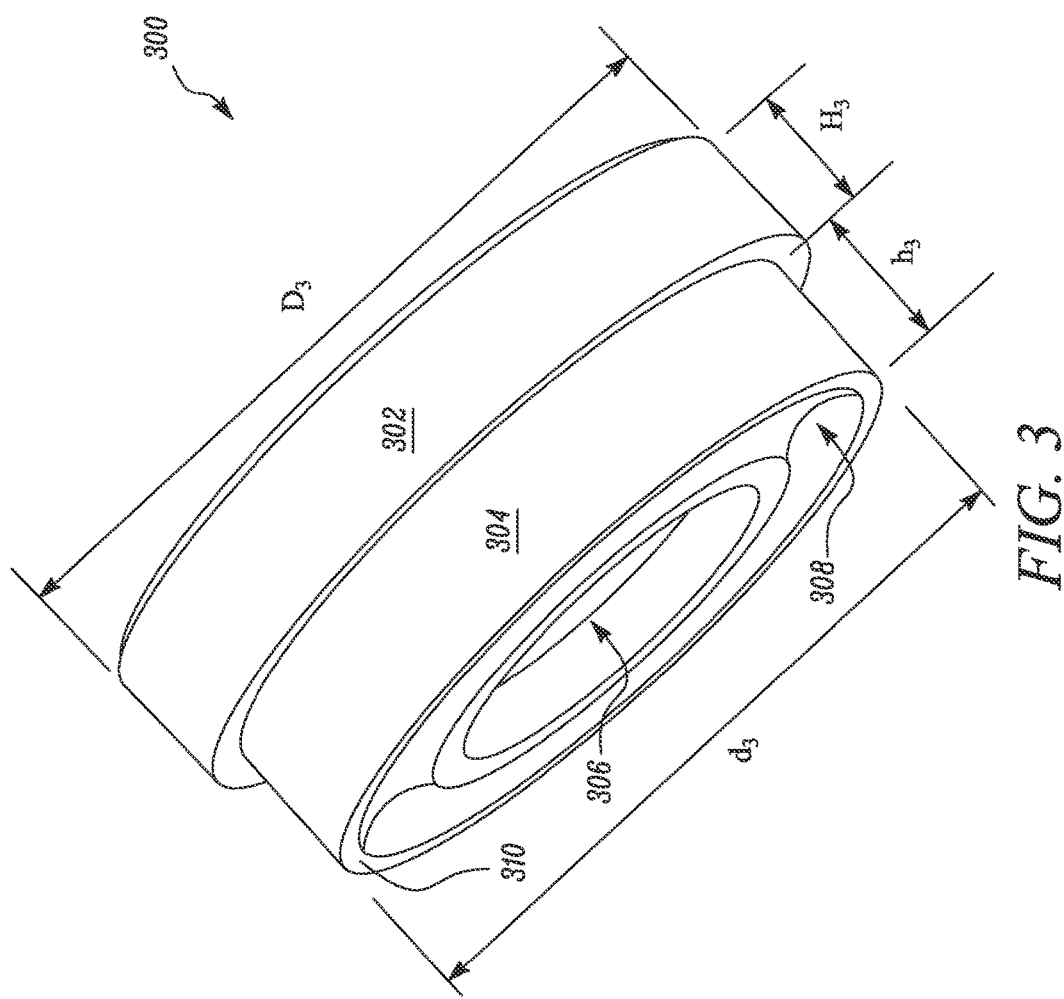
FIGS. 3-8 are perspective views of the boss, according to various embodiments of the present disclosure.

Referring to FIG. 3, the boss 300 has a circular cross-section. The boss 300 may be a unitary structure having a two-tiered design including a first tier 302 and a second tier 304, such that the second tier 304 extends in an axial direction from the first tier 302. Although the boss 300 is shown to have the first and second tiers 302, 304 in the accompanying figures, the boss 300 may include any number of additional tiers based on the application. Further, the boss 300 includes a through hole 306 defined by an inner diameter of the boss 300. The through hole 306 is configured to receive the NOx sensor 130 therein. The NOx sensor 130 may be coupled to the boss 300 using any attachment method known in the art including, but not limited to, welding, brazing, bolting, screw fitting, and adhesion.

Further, each of the first and second tiers 302, 304 may be defined by an outer diameter, hereinafter referred to as a first diameter $D_3$ and a second diameter $d_3$ respectively. The first and second tiers 302, 304 have a first height $H_3$ and a second height $h_3$ respectively. In the illustrated embodiment, the first height $H_3$ is greater than the second height $h_3$. In another example, the second height $h_3$ may be greater than the first height $H_3$. Alternatively, the first height $H_3$ and second height $h_3$ may be equal.

Referring now to FIG. 2, the first tier 302 is configured to be seated onto an exterior surface 202 of the exhaust outlet 116. Condensed water may accumulate on inner surfaces of various parts of the aftertreatment system 100, including the exhaust outlet 116. Further, exhaust gases may contain certain amount of water vapor which may deposit on an inner surface 204 of the exhaust outlet 116. Sometimes, water may seep into the exhaust outlet 116 and contact the sensing element of the NOx sensors 130. The condensed water and/or entrained water may contact the sensing element of the NOx sensor 130. This may damage the NOx sensor 130 and affect an overall working of the aftertreatment system 100. Accordingly, the present disclosure contemplates providing a boss 300 which includes a condensation protection feature to direct water away from the NOx sensor 130.

As shown in FIG. 3, the condensation protection feature of the boss 300 may be embodied as a concave channel 308. The concave channel 308 may include a concentric depression provided on a lower surface 310 of the second tier 304. In a situation wherein the boss 300 is subject to contact with water or any form of condensation, the water on the inner surface 204 of the exhaust outlet 116 may trickle down the first and second heights $H_3$, $h_3$ of the boss 300. Owing to the depth of the concave channel 308, the water may not find a surface to reach the NOx sensor 130, causing the water to drip into the exhaust outlet 116.

Figure 4:
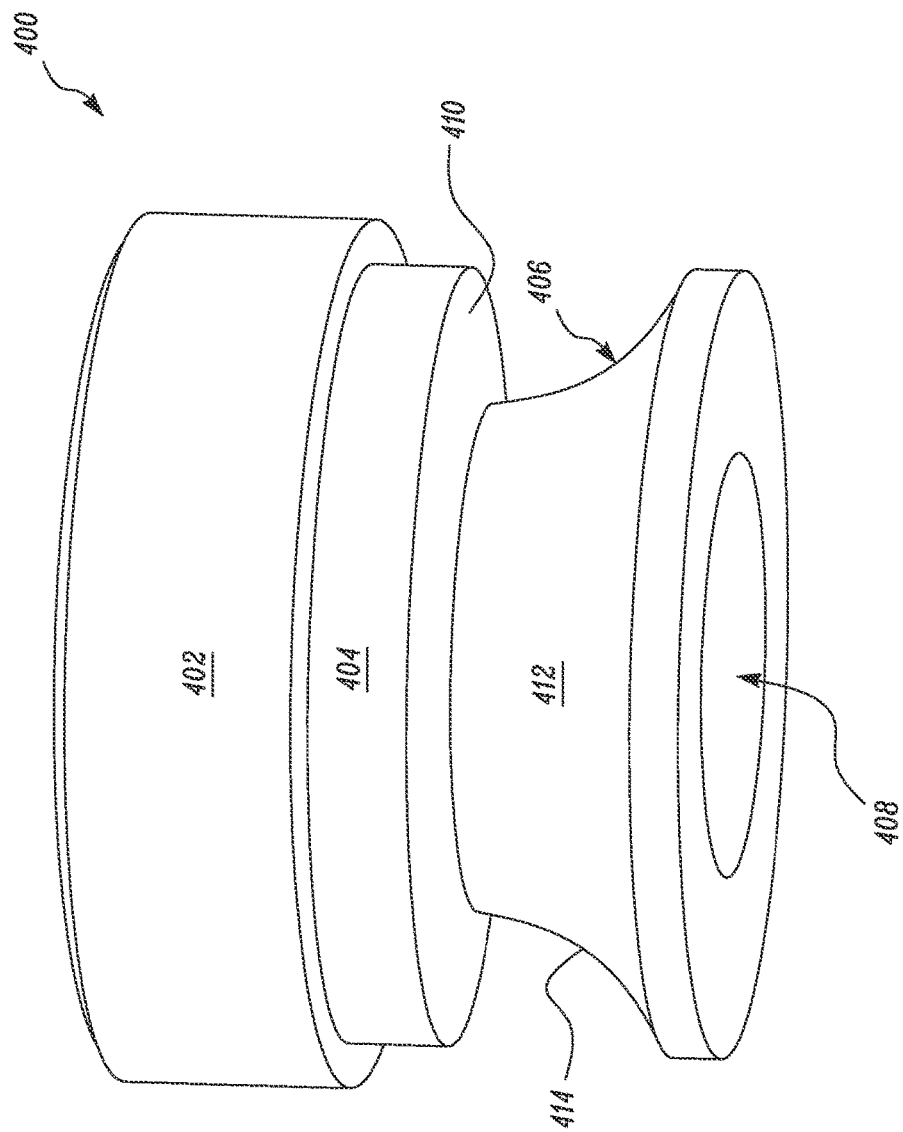

FIG. 4 illustrates an alternate embodiment of the boss 400. In this embodiment, the condensation protection feature of the boss 400 is embodied as a trumpet shaped section 406, having a diameter that gradually increases from the second tier 404 towards a free end of the boss 400. The trumpet shaped section 406 disclosed herein is affixed to or extends from the lower surface 410 of the second tier 404. The trumpet shaped section 406 includes a through hole 408 communicating with the through hole of the boss 400.

The trumpet shaped section 406 has a sidewall 412. As shown in the accompanying figures, an outer face 414 of the sidewall 412 has a concave configuration. The concave configuration of the trumpet shaped section 406 provides a surface for the water to slide thereon and be directed away from the NOx sensor 130. In an alternate embodiment (not shown), the outer face 414 of the sidewall 412 may have a flat configuration. The trumpet shaped section 406 may be formed as a separate piece and affixed to the second tier 404 of the boss 400 using known attachment methods. In another example, the first tier 402, the second tier 404 and the trumpet shaped section 406 may be formed as a single unit.

Figure 5:
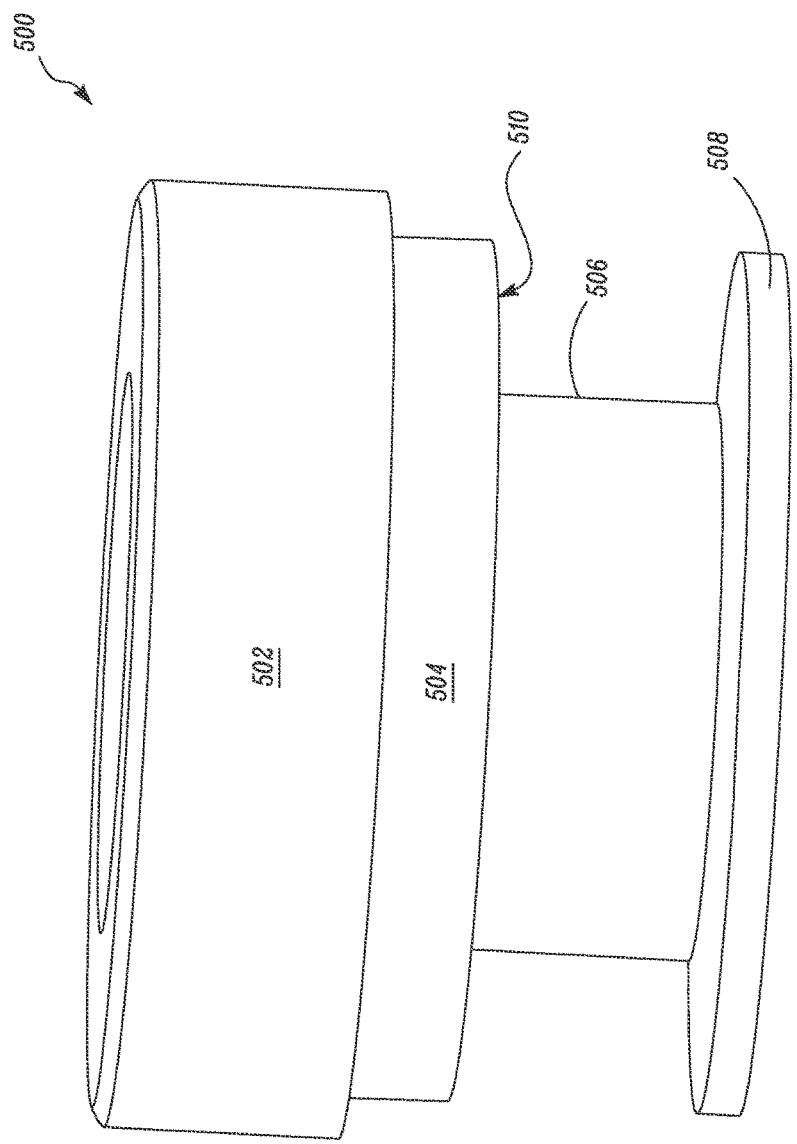
Figure 6:
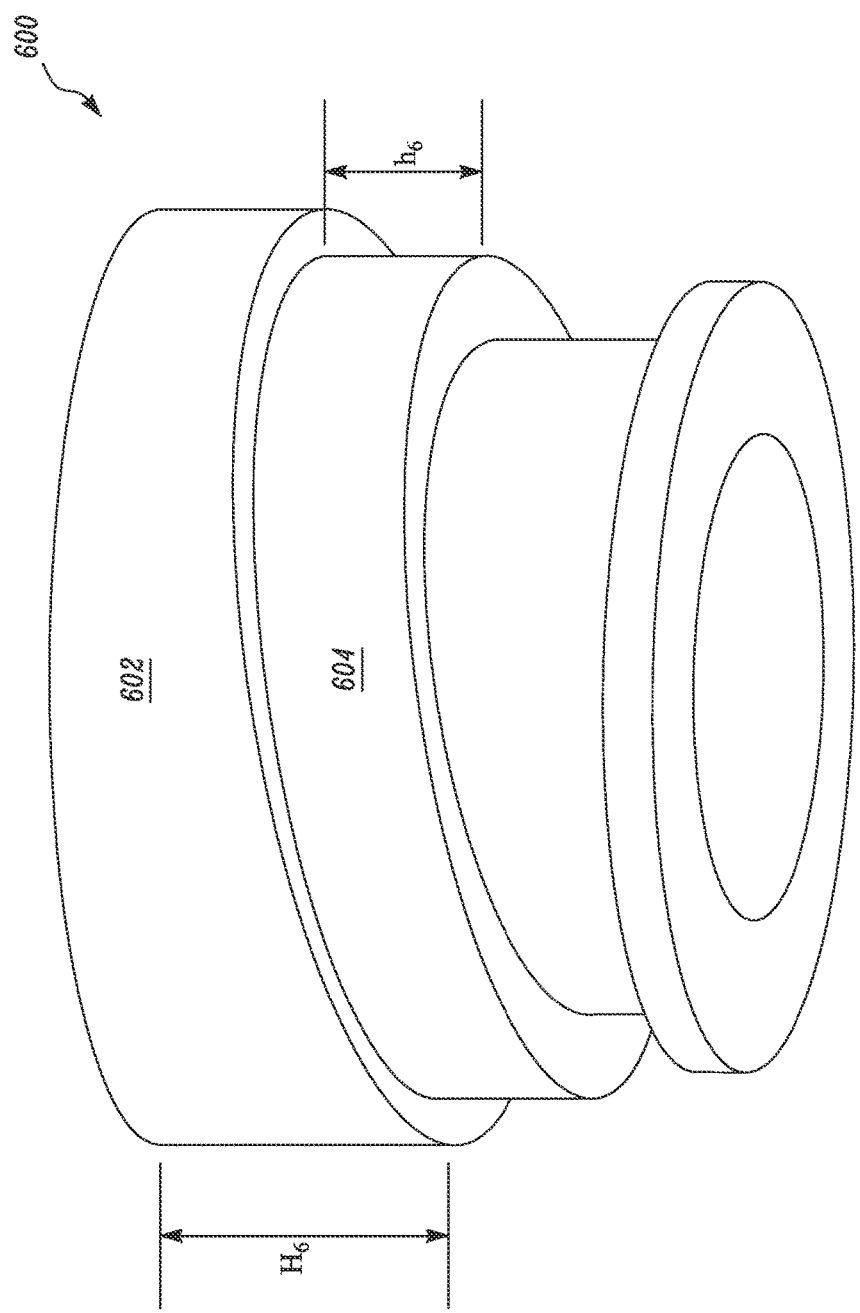

Referring to FIG. 5, the boss 500 having the first and second tiers 502, 504 includes the condensation protection feature embodied as a cylindrical shaped extension 506. The cylindrical shaped extension 506 projects axially from a lower surface 510 of the second tier 504. Also, a flange 508 may extend radially from a lower end of the cylindrical shaped extension 506. The flange 508 of the cylindrical shaped extension 506 may direct the water away from the NOx sensor 130. In an alternate embodiment, as shown in FIG. 6, the boss 600 may include the first tier 602 and the second tier 604, such that the first height $H_6$ and/or the second height $h_6$ may be tapering.

Figure 7:
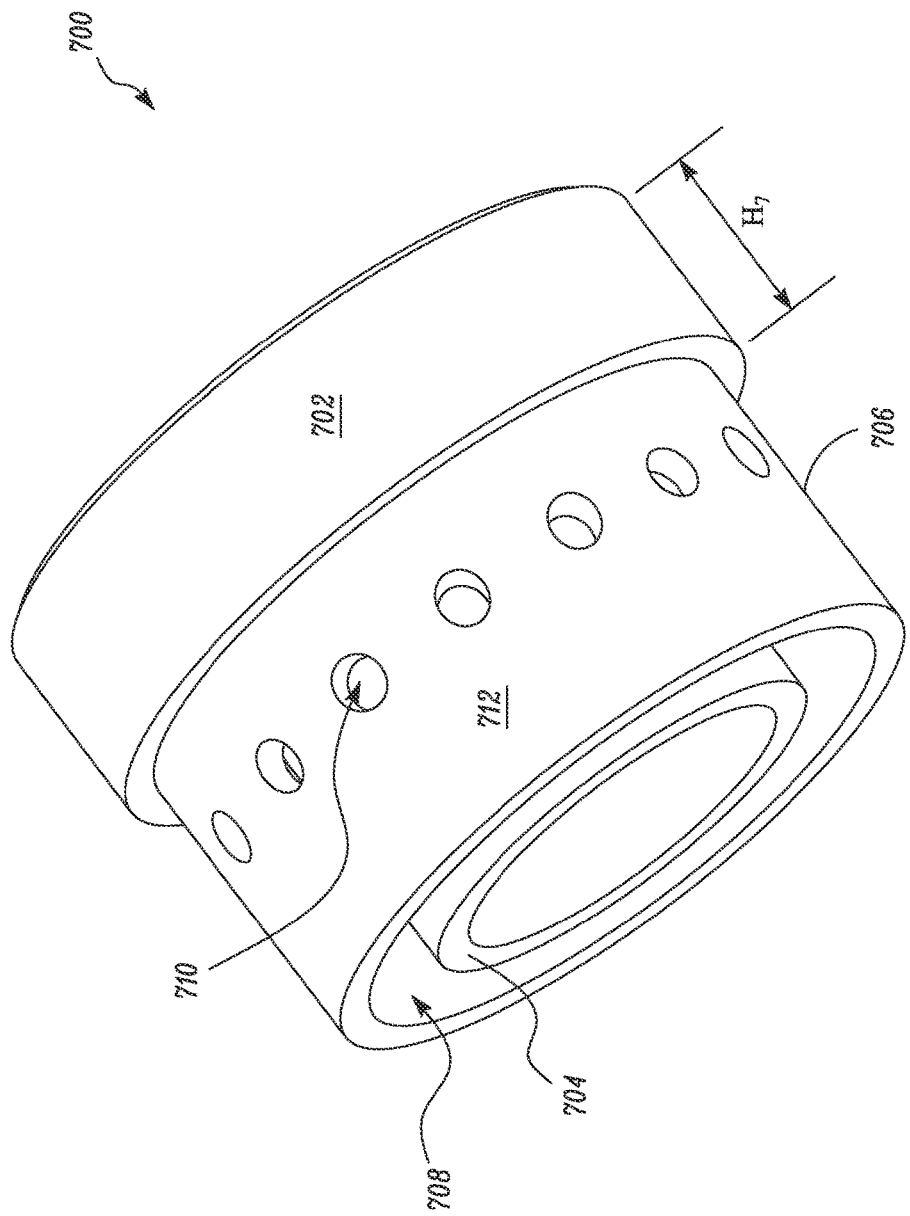

Referring to FIG. 7, the condensation protection feature of the boss 700 may be embodied as a ring shaped extension 706. The ring shaped extension 706 projects axially from the first tier 702 of the boss 700. Further, the ring shaped extension 706 is configured to surround the second tier 704 of the boss 700 forming a space 708 therebetween. Moreover, a height of the ring shaped extension 706 may be equal to or lesser than the second height of the boss 700.

A plurality of through holes 710 may be provided on a sidewall 712 of the ring shaped extension 706. The water entering the exhaust outlet 116 may trickle down the first height $H_7$ of the boss 700 and further over the outer face of the sidewall 712 of the ring shaped extension 706. The water may then enter into the space 708 via the through holes 710 and drip into the exhaust outlet 116.

Figure 8:
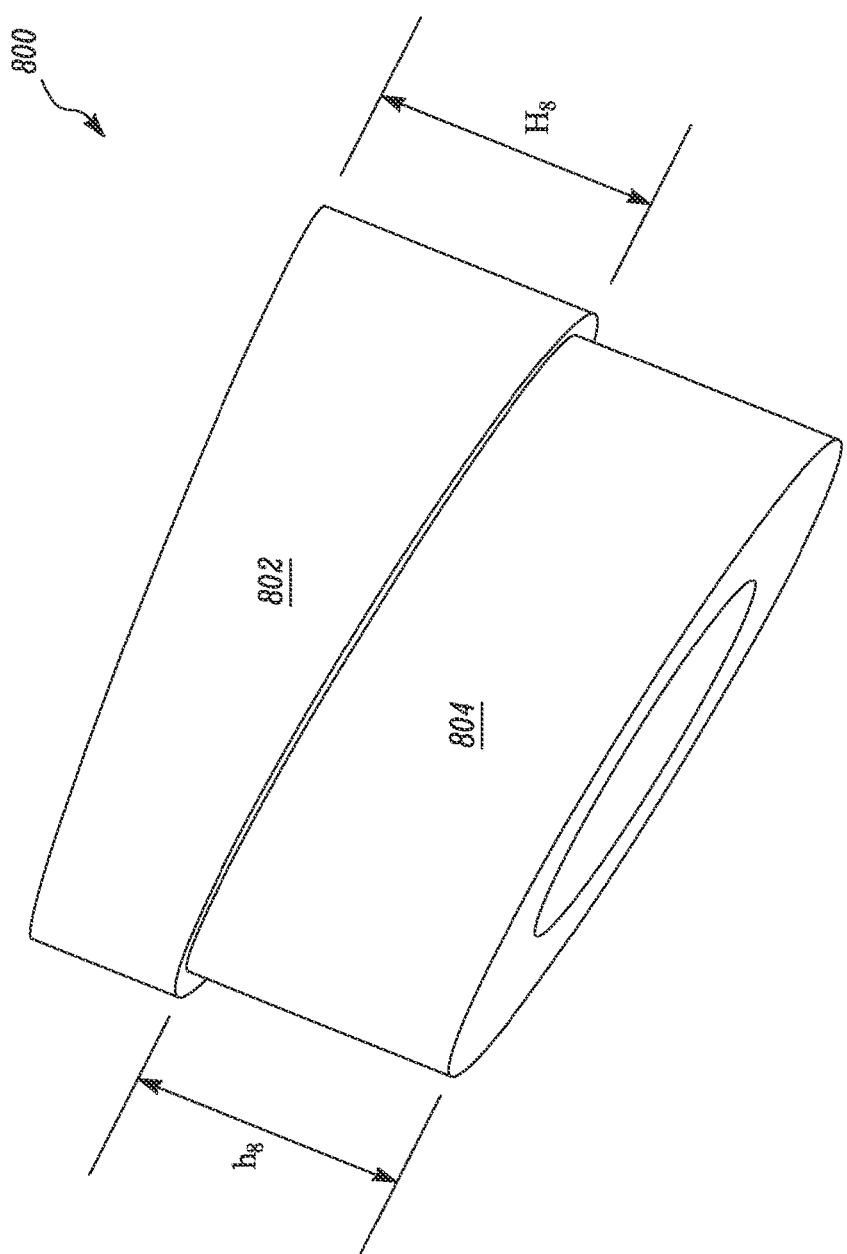

Referring to FIG. 8, the boss 800 may include the first and second tiers 802, 804, such that the first and second heights $H_8$, $h_8$ of the first and second tier 802, 804 respectively are tapering. On assembly, the boss 800 is designed such that the sensing vector of the NOx sensor 130 provided therein may form an angle with the centerline A-A of the exhaust outlet 116. The boss 800 may additionally include any one or a combination of the condensation protection features explained with reference to FIGS. 3-7.

The NOx sensor 130 may be mounted in a manner such that the sensing vector is perpendicular or inclined with respect to the centerline A-A of the exhaust outlet 116 based on an orientation of the exhaust outlet 116. Further, the shape of the exhaust outlet 116 may vary and accordingly, the boss 300, 400, 500, 600, 700 may be positioned within a pocket or protuberance of the exhaust outlet 116.

It should be noted that the boss 300, 400, 500, 600, 700, 800 of the present disclosure may be made of a material that exhibits an ability to sustain high temperatures of the exhaust gases flowing through the exhaust outlet 116. Further, the material of the boss 300, 400, 500, 600, 700, 800 is chosen such that it is easily weldable. Accordingly, the boss 300, 400, 500, 600, 700, 800 may be made of any suitable metal known to a person of ordinary skill in the art, for example steel or an alloy of steel.

INDUSTRIAL APPLICABILITY

During operation of the engine, the exhaust gas flowing through various portions of the aftertreatment system, for example, the exhaust outlet may contain water vapor. The water vapor may condense on the inner surfaces of the exhaust outlet. Further, while starting of the engine, the water vapor may condense on the inner surface of the exhaust outlet. Sometimes, rainwater may also enter the exhaust outlets and flow along the inner surface of the exhaust outlets. The condensed and/or the entrained water may contact with the NOx sensor disposed within the exhaust outlet and may damage the NOx sensor. For example, the water contacting the heated ceramic sensing element may lead to fouling and a possibility of soot contamination of the sensing element. Another possible failure mode of the NOx sensor may be a cracking of the sensing element due to thermal shock.

The NOx sensor may need to be replaced, as a damaged or faulty NOx sensor may lead to an incorrect NOx concentration detection, further affecting an overall working of the aftertreatment system. Periodic replacement of the NOx sensor may lead to an unnecessary increase in an operational cost The present disclosure relates to the boss 300, 400, 500, 600, 700, 800 configured to mount the NOx sensor 130 in the exhaust outlet 116. The boss 300, 400, 500, 600, 700, 800 includes the condensation protection feature, wherein the condensation protection feature is configured to direct the water vapor and/or entrained water away from the NOx sensor 130, thereby protecting the NOx sensor 130 and controlling damage thereof. The boss 300, 400, 500, 600, 700, 800 disclosed herein does not affect the sensing capabilities of the NOx sensor 130 and is a cost-effective solution. Further, the boss 300, 400, 500, 600, 700, 800 may be readily incorporated into a variety of aftertreatment system designs. It should be noted that the described sensor mounting structure is not limited to the mounting of the NOx sensor, and may be utilized in connection with mounting of other sensors, for example, $O_2$ sensors and ammonia sensors.

While aspects of the present disclosure have been particularly shown and described with reference to the embodiments above, it will be understood by those skilled in the art that various additional embodiments may be contemplated by the modification of the disclosed machines, systems and methods without departing from the spirit and scope of what is disclosed. Such embodiments should be understood to fall within the scope of the present disclosure as determined based upon the claims and any equivalents thereof.

What is claimed is:
1. A boss configured to mount a nitrous oxide sensor in an exhaust conduit, the boss comprising:
   a longitudinal axis extending from a first end of the boss to a tip end of the boss, the first end of the boss being configured to be positioned outside the exhaust conduit and the tip end of the boss being configured to be positioned in an interior space defined within the exhaust conduit;

a tubular first tier positioned about the longitudinal axis and extending along the longitudinal axis from the first end to a second end, the first tier configured to contact with an exterior surface of the exhaust conduit, and being defined by a first outer diameter and a first height along a direction of the longitudinal axis;

a tubular second tier positioned about the longitudinal axis and extending along the longitudinal axis from the second end of the first tier to a third end configured to be disposed within the interior space, the second tier being defined by a second diameter and a second height along the direction of the longitudinal axis, the second diameter sized smaller than the first diameter; and a flange extending radially outward from the tip end of the boss in a direction away from the longitudinal axis, the flange being a condensation protection feature configured to direct condensation away from the nitrous oxide sensor.

2. The boss of claim 1, wherein the first height of the first tier is greater than the second height of the second tier.

3. The boss of claim 1, wherein the condensation protection feature includes a cylindrical shaped third tier attached to the second tier and extending from the third end of the second tier to the tip end of the boss.

4. The boss of claim 1, further including a through-hole extending from the first end to the tip end.

5. The boss of claim 4, further including the nitrous oxide sensor positioned in the through-hole.

6. The boss of claim 1, wherein the boss includes steel or an alloy of steel.

7. An exhaust conduit comprising:
an exterior surface having an opening thereon;
a nitrous oxide sensor extending into an interior space defined within the exhaust conduit through the opening; and
a boss disposed within the opening and supporting the nitrous oxide sensor therein, the boss extending from a first end positioned outside the exhaust conduit to a tip end positioned within the interior space, the boss comprising:
  a first tier mounted in contact with the exterior surface of the exhaust conduit, the first tier being positioned circumferentially about the sensor and extending from the first end of the boss towards the interior space;
  a second tier positioned circumferentially about the sensor and extending from the first tier, into the interior space of the exhaust conduit towards the tip end of the boss; and
  a flange circumferentially disposed about the sensor and extending radially outward from the tip end of the boss in a direction away from the sensor, the flange being a condensation protection feature configured to direct condensation away from the nitrous oxide sensor.

8. The boss of claim 7, further including a through-hole extending from the first end to the tip end, wherein the nitrous oxide sensor extends into the interior space through the through-hole.

9. The boss of claim 7, wherein the first tier extends from the first end to a second end positioned in contact with the exhaust conduit, and the second tier from the second end to a third end positioned in the interior space.

10. The boss of claim 9, further including a third tier extending from the third end to the tip end of the boss.

11. The boss of claim 10, wherein an outer diameter of the third tier is less than an outer diameter of the second tier, and an outer diameter of the second tier is less than an outer diameter of the first tier.

12. A boss configured to mount a nitrous oxide sensor in an exhaust conduit, the boss comprising:
a through-hole extending longitudinally from a first end of the boss to a tip end of the boss, the first end being configured to be positioned outside the exhaust conduit and the tip end being configured to be positioned in an interior space defined within the exhaust conduit;
a nitrous oxide sensor extending into the interior space of the exhaust conduit through the through-hole on the boss;
a first tier circumferentially disposed about the sensor and extending towards the exhaust conduit from the first end to a second end, the first tier having a first outer diameter;
a second tier circumferentially disposed about the sensor and extending from the second end to a third end positioned within the interior space of the exhaust conduit, the second tier having a second outer diameter smaller than the first outer diameter;
a third tier circumferentially disposed about the sensor and extending from the third end to the tip end of the boss, the third tier having a third outer diameter smaller than the second outer diameter; and
a flange circumferentially disposed about the sensor and extending radially outward from the tip end of the boss in a direction away from the sensor.

13. The boss of claim 12, wherein a height of the first tier and the third tier is greater than a height of the second tier.

14. The boss of claim 12, wherein the boss includes steel or an alloy of steel.

15. The boss of claim 12, wherein the first tier, second tier, and the third tier are integral parts of the boss.

* * * * *